(12) United States Patent
Kvietok et al.

(10) Patent No.: US 8,016,207 B2
(45) Date of Patent: *Sep. 13, 2011

(54) SYSTEMS AND DEVICES FOR EMITTING VOLATILE COMPOSITIONS

(75) Inventors: Frank Andrej Kvietok, Aurora, CO (US); Eileen Marie St. Pierre, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/124,962

(22) Filed: May 9, 2005

(65) Prior Publication Data

US 2005/0201944 A1 Sep. 15, 2005

Related U.S. Application Data

(63) Continuation of application No. 10/417,456, filed on Apr. 16, 2003, now abandoned, which is a continuation-in-part of application No. 09/904,019, filed on Jul. 12, 2001, now abandoned.

(60) Provisional application No. 60/251,067, filed on Dec. 4, 2000.

(51) Int. Cl.
*A61L 9/00* (2006.01)
(52) U.S. Cl. ............ 239/34; 239/44; 422/123; 422/124
(58) Field of Classification Search ............... 422/4, 5, 422/123, 124, 105; 261/30; 239/56, 57, 239/34, 44
See application file for complete search history.

(56) References Cited

U.S. PATENT DOCUMENTS

| 1,944,821 | A | 1/1934 | Blaise |
| 2,176,345 | A | 10/1939 | Hurwitt |
| 2,611,068 | A | 9/1952 | Wellens |
| 2,715,056 | A | 8/1955 | Wilson |
| 2,898,649 | A | 8/1959 | Murray |
| 3,028,100 | A | 4/1962 | Xenakis et al. |
| 3,091,396 | A | 5/1963 | Curtin |
| 3,431,393 | A | 3/1969 | Katsuda |
| 3,440,589 | A | 4/1969 | Minks |
| 3,724,756 | A | 4/1973 | Maltenfort |

(Continued)

FOREIGN PATENT DOCUMENTS

CA 2329605 7/2001

(Continued)

OTHER PUBLICATIONS

PCT International Search Report, Mailed Sep. 22, 2004, 4 Pages.

(Continued)

*Primary Examiner* — Sean E Conley
(74) *Attorney, Agent, or Firm* — Amy I Ahn-Roll; Brent M Peebles; Leonard W Lewis

(57) ABSTRACT

Methods and devices for emitting volatile materials are disclosed. In some embodiments, methods and devices for emitting two or more fragrance compositions are disclosed. In one non-limiting embodiment of a device, the device has a housing, and the housing is supported on an electrical outlet by a plug at least indirectly joined to the housing. The device contains a first volatile composition and a second volatile composition. The first volatile composition is emmitted in an alternating period relative to said second volatile composition. In one embodiment of the method, the volatile compositions are alternately emitted during periods that are greater than 15 minutes and less than 2 hours.

31 Claims, 6 Drawing Sheets

U.S. PATENT DOCUMENTS

| | | | |
|---|---|---|---|
| 3,780,260 | A | 12/1973 | Elsner |
| 4,166,087 | A | 8/1979 | Cline et al. |
| 4,181,255 | A | 1/1980 | Cort |
| 4,346,059 | A | 8/1982 | Spector |
| 4,467,177 | A | 8/1984 | Zobele |
| 4,494,926 | A | 1/1985 | Riha |
| 4,556,539 | A * | 12/1985 | Spector .................. 422/125 |
| 4,595,564 | A | 6/1986 | Spector et al. |
| 4,603,030 | A | 7/1986 | McCarthy |
| 4,621,768 | A | 11/1986 | Lhoste et al. |
| 4,629,604 | A * | 12/1986 | Spector .................. 422/124 |
| 4,631,387 | A | 12/1986 | Glucksman |
| 4,663,315 | A | 5/1987 | Hasegawa et al. |
| 4,739,928 | A | 4/1988 | O'Neil |
| 4,745,705 | A | 5/1988 | Yamamoto et al. |
| 4,769,528 | A | 9/1988 | Von Philipp et al. |
| 4,795,883 | A | 1/1989 | Glucksman et al. |
| 4,798,935 | A | 1/1989 | Pezaris |
| 4,804,821 | A | 2/1989 | Glucksman |
| 4,857,240 | A | 8/1989 | Kearnes et al. |
| 4,913,350 | A | 4/1990 | Purzycki |
| 4,952,024 | A | 8/1990 | Gale |
| 4,968,487 | A * | 11/1990 | Yamamoto et al. ........ 422/125 |
| 5,000,383 | A | 3/1991 | van der Heijden |
| 5,038,394 | A | 8/1991 | Hasegawa et al. |
| 5,095,647 | A | 3/1992 | Zobele et al. |
| 5,111,477 | A | 5/1992 | Muderlak |
| 5,114,625 | A | 5/1992 | Gibson |
| 5,115,975 | A | 5/1992 | Shilling |
| 5,222,186 | A | 6/1993 | Schimanski et al. |
| 5,264,681 | A | 11/1993 | Nozaki et al. |
| 5,290,546 | A | 3/1994 | Hasegawa et al. |
| 5,402,517 | A | 3/1995 | Gillett et al. |
| 5,565,148 | A * | 10/1996 | Pendergrass, Jr. .......... 261/30 |
| 5,591,409 | A | 1/1997 | Watkins |
| 5,622,314 | A | 4/1997 | Eason |
| 5,645,052 | A | 7/1997 | Kersey |
| 5,647,053 | A | 7/1997 | Schroeder et al. |
| 5,669,767 | A | 9/1997 | Bureau et al. |
| 5,725,152 | A | 3/1998 | Akyu |
| 5,727,186 | A | 3/1998 | Shervington et al. |
| 5,749,519 | A | 5/1998 | Miller |
| 5,749,520 | A | 5/1998 | Martin et al. |
| 5,805,768 | A | 9/1998 | Schwartz et al. |
| 5,840,246 | A | 11/1998 | Hammons et al. |
| 5,875,968 | A | 3/1999 | Miller et al. |
| 5,903,710 | A | 5/1999 | Wefler et al. |
| 5,906,298 | A | 5/1999 | Ward |
| 5,909,845 | A | 6/1999 | Greatbatch et al. |
| 5,945,094 | A | 8/1999 | Martin et al. |
| 5,976,503 | A | 11/1999 | Martin et al. |
| 6,044,202 | A | 3/2000 | Junkel |
| 6,085,026 | A | 7/2000 | Hammons et al. |
| 6,152,379 | A | 11/2000 | Sorgenfrey |
| 6,236,807 | B1 | 5/2001 | Ruffolo et al. |
| 6,254,065 | B1 | 7/2001 | Ehrensperger et al. |
| 6,278,840 | B1 | 8/2001 | Millan |
| 6,285,830 | B1 | 9/2001 | Millan |
| 6,354,513 | B1 | 3/2002 | Millan |
| 6,361,752 | B1 | 3/2002 | Demarest et al. |
| 6,371,451 | B1 | 4/2002 | Choi |
| 6,446,384 | B2 | 9/2002 | Pedrotti et al. |
| 6,446,583 | B2 | 9/2002 | Vieira |
| 6,465,420 | B1 | 10/2002 | Perring et al. |
| 6,466,739 | B2 | 10/2002 | Ambrosi et al. |
| 6,487,367 | B2 | 11/2002 | Vieira |
| 6,501,906 | B2 | 12/2002 | Vieira |
| 6,563,091 | B2 | 5/2003 | Vieira |
| 6,567,613 | B2 | 5/2003 | Rymer |
| RE38,150 | E | 6/2003 | Greatbatch et al. |
| 6,580,875 | B2 | 6/2003 | Rymer |
| 6,603,924 | B2 | 8/2003 | Brown et al. |
| 6,619,560 | B1 | 9/2003 | Chun |
| 6,659,301 | B2 | 12/2003 | Fellows et al. |
| 6,663,838 | B1 | 12/2003 | Soller et al. |
| 6,697,571 | B2 | 2/2004 | Triplett et al. |
| 6,859,615 | B2 | 2/2005 | Yip et al. |
| 7,223,361 | B2 | 5/2007 | Kvietok et al. |
| 7,344,123 | B2 | 3/2008 | Pankhurst et al. |
| 2001/0012495 | A1 | 8/2001 | Furner et al. |
| 2001/0020450 | A1 | 9/2001 | Vieira |
| 2002/0036358 | A1 | 3/2002 | Watkins |
| 2002/0066798 | A1* | 6/2002 | Laudamiel-Pellet et al. ... 239/34 |
| 2002/0066967 | A1 | 6/2002 | Bartsch et al. |
| 2002/0068010 | A1 | 6/2002 | Laudamiel-Pellet et al. |
| 2002/0076214 | A1 | 6/2002 | Vieira |
| 2002/0090318 | A1 | 7/2002 | Challand et al. |
| 2002/0158351 | A1* | 10/2002 | Wohrle .................. 261/142 |
| 2002/0159916 | A1 | 10/2002 | Whitby et al. |
| 2003/0005620 | A1 | 1/2003 | Ananth et al. |
| 2004/0033171 | A1 | 2/2004 | Kvietok et al. |
| 2004/0285511 | | 2/2004 | Kvietok et al. |
| 2004/0265164 | A1 | 12/2004 | Woo et al. |
| 2005/0201944 | A1 | 9/2005 | Kvietok et al. |
| 2008/0069725 | A1 | 3/2008 | Kvietok et al. |

FOREIGN PATENT DOCUMENTS

| | | | |
|---|---|---|---|
| DE | 201 07811 U1 | | 10/2001 |
| EP | 0238 983 A2 | | 9/1987 |
| EP | 0 736 248 A1 | | 10/1996 |
| EP | 0 740 941 A1 | | 11/1996 |
| EP | 0 511 853 B1 | | 12/1997 |
| EP | 0 911 041 A2 | | 4/1998 |
| EP | 0 962 132 A1 | | 12/1999 |
| EP | 0 911 041 A3 | | 9/2000 |
| EP | 0 942 648 B9 | | 1/2002 |
| EP | 0 943 344 B1 | | 9/2002 |
| EP | 0 962 132 B1 | | 5/2003 |
| ES | 1 015 255 | | 6/1991 |
| GB | 2 279010 A | | 12/1994 |
| GB | 2347860 A | * | 9/2000 |
| GB | 2 358 802 A | | 8/2001 |
| GB | 2 375 710 A | | 11/2002 |
| JP | 64-39745 U | | 3/1989 |
| JP | 03-14 7731 | | 6/1991 |
| JP | 03-108134 | | 8/1991 |
| JP | 09 047499 A | | 2/1997 |
| JP | 09-201155 A | | 8/1997 |
| JP | 11000391 A | | 1/1999 |
| WO | WO 90/13359 A1 | | 11/1990 |
| WO | WO 94/15650 A1 | | 7/1994 |
| WO | WO 98/00177 | | 1/1998 |
| WO | WO 98/19526 A1 | | 5/1998 |
| WO | WO 98/58692 A1 | | 12/1998 |
| WO | WO 00/48922 A1 | | 8/2000 |
| WO | WO 01/05442 A1 | | 1/2001 |
| WO | WO 02/17977 A3 | | 3/2002 |
| WO | WO 02/060494 A1 | | 8/2002 |
| WO | WO 03/028775 A1 | | 4/2003 |
| WO | WO 03/103387 A2 | | 12/2003 |
| WO | WO 2004/002542 A1 | | 1/2004 |

OTHER PUBLICATIONS

Corrected Request for Inter Partes Reexamination of US Patent 7,223,361 B2.

Inter Partes Reexamination Communication for U.S. Appl. No. 95/000,377.

Office Action for U.S. Appl. No. 95/000,377, date mailed Nov. 20, 2008.

Response to Notice Re Defective Paper in Inter Partes Reexamination for U.S. Appl. No. 95/000,377, dated Feb. 25, 2009.

Comments By Third Party Requester for U.S. Appl. No. 95/000,377, dated Mar. 25, 2009.

Office Action for U.S. Appl. No. 95/000,377, date mailed Dec. 09, 2009.

Response to Office Action-Closing for U.S. Appl. No. 95/000,377, dated Jan. 11, 2010.

Comments By Third Party Requester, for U.S. Appl. No. 95/000,377, dated Feb. 10, 2010.

Office Action for U.S. Appl. No. 95/000,377, dated Mar. 22, 2010.

Response to Office Action-Closing for U.S. Appl. No. 95/000,377, dated Apr. 22, 2010.

Comments By Third Party Requester, for U.S. Appl. No. 95/000,377, dated May 24, 2010.

Appeal Brief for U.S. Appl. No. 95/000,377, filed Sep. 16, 2010.
Comments By Third Party Requester, for U.S. Appl. No. 95/000,377, dated Oct. 13, 2010.
Office Action for U.S. Appl. No. 95/000,377, dated Nov. 24, 2010.
Response to Office Action-Closing for U.S. Appl. No. 95/000,377, dated Dec. 22, 2010.
Comments By Third Party Requester, for U.S. Appl. No. 95/000,377, dated Jan. 22, 2011.
U.S. Appl. No. 95/000,377, filed Jun. 18, 2008, Frank Andrej Kvietok.

* cited by examiner

SYSTEMS AND DEVICES FOR EMITTING VOLATILE COMPOSITIONS

CROSS REFERENCE TO RELATED PATENT APPLICATIONS

This application is a continuation-in-part of U.S. patent application Ser. No. 09/904,019, filed Jul. 12, 2001, which claims the benefit of the filing dates of, and is a continuation-in-part of: PCT application Ser. No. US00/20499, filed Jul. 27, 2000, and U.S. patent application Ser. Nos. 09/730,226; 09/730,261; and 09/730,333, all filed Dec. 5, 2000, the disclosures of which are all incorporated by reference herein.

FIELD OF THE INVENTION

The present invention relates to methods and devices for emitting volatile compositions. In some embodiments, the invention relates to a method and devices for emitting two or more distinct volatile compositions.

BACKGROUND OF THE INVENTION

It is generally known to use an electrical device to evaporate a perfume and/or fragrance composition into a space, particularly a domestic space, e.g., a living room, to provide a pleasant aroma. There are a variety of such devices on sale, for example the AIRWICK® Diffuser ACTIF® (manufactured by Reckitt Benckiser) or the AMBI-PUR® fragrance diffuser (manufactured by Sara Lee). Generally, these devices consist of a perfume or fragrance source, an electrical heater and a power supply. By the application of heat to the perfume or fragrance source, there will be a continuous supply of the perfume or fragrance to the space in which the device is placed.

The problem with this arrangement is that a person occupying the space will quickly become accustomed to the perfume or fragrance and, after a while, will not perceive the fragrance strength as being as intense and may not notice it at all. This is a well-known phenomenon called habituation. A solution to this problem has been sought.

One effort to deal with this problem is described in U.S. patent application Publication No. US 2002/0159916 A1, Whitby, et al. The Whitby, et al. patent application discloses a method and device adapted to provide to a space, two or more fragrance compositions, at least one of which fragrance compositions is provided periodically. The method and device may provide a continuous supply of a first-fragrance composition and a periodic-supply of a second fragrance composition. The fragrance composition(s) may be vaporized by heating and may include deodorant and/or insecticidal compounds. The fragrance compositions are preferably chosen such that the two fragrance compositions contrast with one another or have different notes. The fragrance composition is generally pulsed from a device which includes a heater. The periodic supply of heat to release the fragrance composition is controlled by providing the device, and particularly the heater, with a controller. The controller is in the form of an electronic circuit. The controller is arranged such that the heater runs for a short period of time, preferably from 15 seconds to 15 minutes with "appropriate intervals of time there between".

The Whitby, et al. patent application, however, appears to be directed primarily to maintaining or sustaining the olfactory impact of the fragrance composition being emitted continuously, rather than to providing to the user noticeable changes in fragrances. In addition, although the Whitby, et al. patent application mentions periodic supply of two or more fragrances, there is no specific teaching of emission patterns or programs dictating the supply of the different fragrances relative to each other so that the users actually experience distinct fragrances rather than one fragrance which is a blend of the two compositions.

SUMMARY OF THE INVENTION

The present invention relates to methods and devices for emitting volatile compositions. In some embodiments, the invention relates to a method and devices for emitting two or more fragrance compositions. There are numerous embodiments of the methods and devices described herein, all of which are intended to be non-limiting examples.

In some embodiments of the method, it may be desirable for those who either experience the emission of the fragrance composition(s), or who are in the presence of the device(s) emitting fragrance composition(s), to experience and/or perceive a pleasant scent all of the time. In other cases, this may not be all of the time, but all of the time that such persons wish to perceive a fragrance. In some embodiments in which the method is used to emit two or more fragrance compositions, it may be desirable to maximize the perceptibility of each of two or more separate and distinct fragrance compositions. Thus, the method can do more than merely prevent habituation to a given fragrance composition. In such embodiments, therefore, it may be desirable for the time for emission of the fragrances not to change too quickly, otherwise, there will not be a perception of two different fragrances, but rather a blended scent. In other embodiments, however, it may also be desirable to provide a blended scent experience, for at least a period of time.

In one embodiment of the method, the volatile compositions are alternately emitted during discrete emission periods that are greater than 15 minutes and less than or equal to 24 hours. The device can automatically switch to alternate the volatile composition being emitted. In other embodiments, the device may emit volatile compositions for periods less than or equal to 15 minutes; or it may emit volatile compositions for periods greater than 24 hours (e.g., 48 hours). Numerous other embodiments are possible.

The method can utilize one or more devices. In one embodiment that emits fragrance composition(s), a single device is used that is a dual scented "plug-in" that switches back and forth between two (or more) scents. This embodiment of the device has a housing, and the housing is supported on an electrical outlet by a plug at least indirectly joined to the housing. The device contains a first volatile composition and a second volatile composition. The first volatile composition is emitted in an alternating period relative to said second volatile composition. Numerous other types of devices are possible. For example, in other embodiments, the method described herein can be carried out by two or more dispensing devices. Such dispensing devices comprise any type of dispensing device, including, but not limited to aerosol sprayers.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE INVENTION

The present invention relates to methods and devices for emitting volatile compositions. In some embodiments, the invention relates to methods and devices for emitting two or more volatile compositions. There are numerous embodiments of the methods and devices described herein, all of which are intended to be non-limiting examples.

The methods for emitting volatile compositions can comprise a variety of different embodiments. The two or more volatile compositions can be fragrance compositions, compositions that function as insecticides, air fresheners, deodorants, aromacology, aromatherapy, insecticides, or any other material that acts to condition, modify, or otherwise charge the atmosphere or to modify the environment. The two or more volatile materials emitted in a given embodiment of the method can be the same type of material (e.g., two or more fragrance compositions), or they can be different types of materials (e.g., fragrance compositions and air fresheners). Deodorants, or malodor control compositions may comprise a material selected from the group consisting of: odor neutralizing materials, odor blocking materials, odor masking materials, and combinations thereof. The methods can emit the volatile compositions in a sequence in which the emission of the different volatile compositions automatically alternates between the different volatile compositions.

The volatile compositions can be emitted in any suitable sequence. The sequence of emission of the volatile compositions can be in a pattern, or it can be random. The term "pattern", as used herein, refers to repeating sequences. In embodiments where the sequence of emission of the different volatile compositions is repeatable, the pattern can be repeated once, or any number of times after the initial sequence. The term "random", as used herein, refers to sequences in which the sequence of emission of the volatile compositions does not repeat in a regular fashion. It is also possible for an emission sequence to comprise a portion of time where the sequence is in a pattern, and a portion of time in which the sequence is random.

Figure 1:
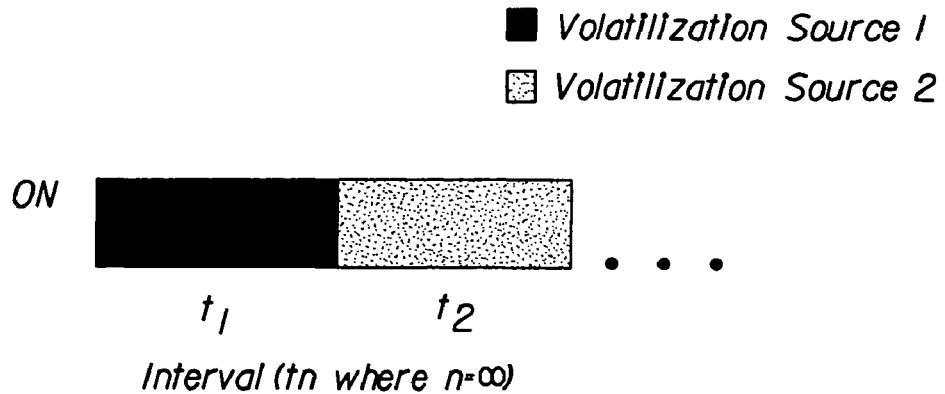
FIG. 1 is a diagram that shows one non-limiting embodiment of an emission program for emitting two volatile compositions.
Figure 2:
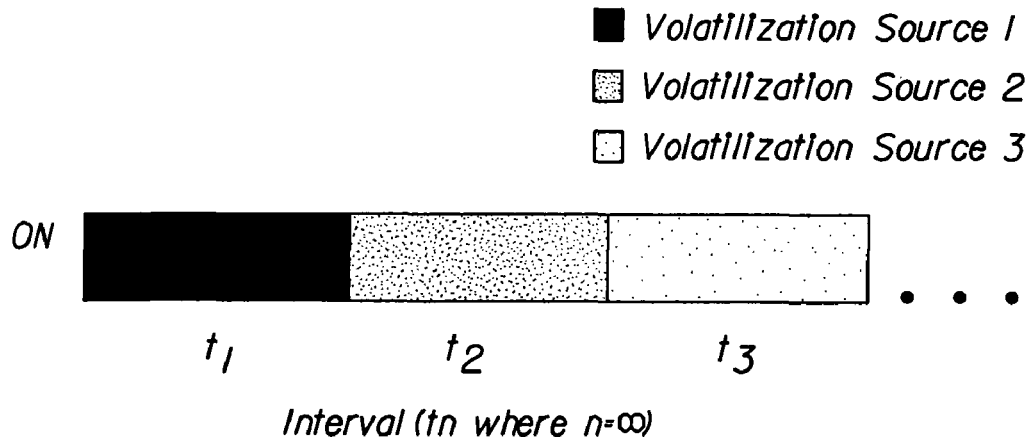
FIG. 2 is a diagram that shows one non-limiting embodiment of an emission program for emitting three (or more) volatile compositions.

In some embodiments, two or more volatile compositions are emitted in an alternating sequence. For example, there can be a first volatile composition and a second volatile composition, and the first volatile composition is emitted in an alternating period relative to said second volatile composition. Thus, if the first volatile composition is designated "1", and the second volatile composition is designated "2", the volatile compositions can be emitted in an alternating pattern as follows: 1, 2, 1, 2, . . . , etc. FIG. 1 shows such an emission program schematically. In FIG. 1, the diagram represents the periods during which that the volatile compositions are being subjected to a source of energy,(or "activated") (for example, if they are in a device which has a heater that heats the compositions, the diagram can designate the periods of time that during which the heaters are on and off). If there are three volatile compositions, they can be emitted in an alternating pattern as follows: 1, 2, 3, 1, 2, 3, . . . , etc. as shown in FIG. 2.

In viewing these figures (and the diagrams which follow), it should be understood that these are non-limiting embodiments. In other embodiments, there need not be a separate volatilization source (such as a heater) for each volatile composition. There can be any suitable number of volatilization sources for the volatile compositions. For example, a single volatilization source can be used to volatilize more than one volatile composition. Such a C volatilization source could, for example, be capable of moving to volatilize the different volatile compositions, or it can be capable of selectively directing energy (e.g., heat) to the different volatile compositions (such as by opening and closing a door or gate between the volatilization source and a given volatile composition). Alternatively, containers can be movable relative to the volatilization source (so that the containers can be selectively moved over a heater, for example).

The term "interval", as used herein, refer to the shortest period of time in the emission sequence. The term "discrete emission period", as used herein, refer to the individual time period that a given volatile material (or combination of volatile materials) is emitted in the emission sequence. This may correspond generally to the period of time that a heater, for example, is turned on for a given volatile material or combination of volatile materials (though there may be a slight lag between the operation of a heater and the emission of a volatile material). The discreet emission periods can also be referred to herein as a first time period, a second time period, etc. (each of which has a beginning and end). It should be understood that it is not necessary that the different volatile compositions be emitted for equal time periods. For example, after one volatile composition is emitted, a different volatile composition can be emitted for a shorter, or alternatively, a longer time period. In another example, the after one volatile composition is emitted, it can be followed by another interval of the same volatile composition before a different volatile composition is emitted. In cases where the different volatile compositions are not emitted for equal time periods, it may be desirable to provide a greater amount of the compositions that are emitted for a longer cumulative time period so that the volatile compositions will be depleted at about the same time. There are numerous possible alternating emission sequences. In the case of three volatile compositions, non-limiting examples of some other possible patterns of emission include, but are not limited to: (1, 2 2 1, 1, 3 3);(1, 2, 3, 3, 2, 1); and (1, 2 2 2 2, 1 1, 3 3 3 3, 1).

In some embodiments of the method, the volatile compositions can be emitted during a discrete emission period that is less than or equal to about 15 minutes, but it may be more desirable for each emission period to be longer than 15 minutes. In the case of scented materials, longer time periods may be more desirable. In one embodiment of the method, the volatile compositions are alternately emitted during discrete periods that are each greater than 15 minutes and less than or equal to about 12 hours, or less than or equal to about 24 hours, or less than or equal to about 48 hours, or more. Every numerical range given throughout this specification will include every narrower numerical range that falls within such broader numerical range, as if such narrower numerical ranges were all expressly written herein. Thus, in another non-limiting embodiment, the volatile compositions are alternately emitted during periods that are greater than 15 minutes, or greater than or equal to about 1 hour, and less than 2 hours. In one embodiment, each volatile composition is emitted for a period of about 72 minutes.

Figure 3:
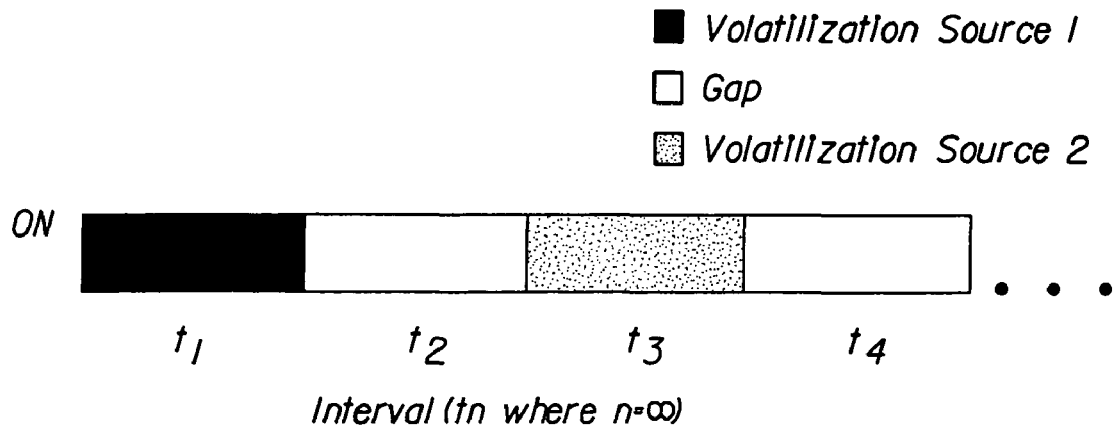
FIG. 3 is a diagram that shows one non-limiting embodiment of an emission program for emitting two (or more) volatile compositions where there is a gap between the emissions of the volatile compositions.
Figure 4:
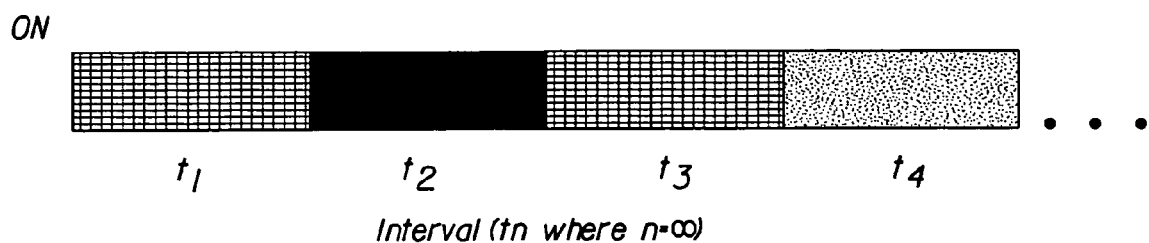
FIG. 4 is a diagram that shows one non-limiting embodiment of an emission program for emitting two (or more) volatile compositions where there is an overlap of the emissions of the volatile compositions.
Figure 5:
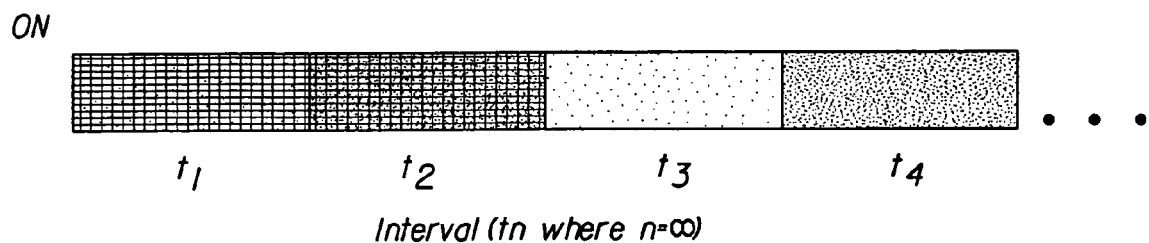
FIG. 5 is a diagram that shows one non-limiting embodiment of an emission program for emitting three (or more) volatile compositions where there is an overlap of the emissions of one volatile composition with the emission of two other volatile compositions.

The volatile compositions may be emitted so that one immediately follows the end of the emission period of the other. In other embodiments, the volatile compositions can be emitted so that there is a gap between the end of the emission period of one of the volatile compositions, and the beginning of the emission period of another volatile composition. FIG. 3 is a diagram that shows one non-limiting embodiment of an emission program for emitting two volatile compositions where there is a gap between the emissions of the volatile compositions where "g" designates a gap. In other embodiments, the volatile compositions can be emitted so that there is an overlap in the emission periods of two, or more volatile compositions. FIG. 4 is a diagram that shows one non-limiting embodiment of an emission program for emitting two volatile compositions where there is an overlap of the emissions of the volatile compositions where the symbol "&" designates an emission period where both volatile compositions are being emitted. FIG. 5 shows one non-limiting embodiment of an emission program for emitting three (or more) volatile compositions where there is an overlap of the emissions of one volatile composition with the emission of two other volatile compositions. In other embodiments, it is possible for one or more of the volatile compositions to be emitted continuously, and another volatile composition to be emitted for periods of time that are greater than 15 minutes.

If it is desirable to have a gap between the end of the emission period of one of the volatile materials, and the beginning of the emission period of another volatile material, the gap can be of any suitable duration. Suitable durations include, but are not limited any periods that are less than or equal to about 30 minutes. However, it is also possible to have gap periods of greater than 30 minutes. If it is desirable to have an overlap in the emission periods of two, or more volatile materials, the overlap can be of any suitable duration. The emission period of a subsequently emitted volatile material may overlap from greater than 0% up to 100% of the time a first volatile material is being emitted. In certain embodiments, for example, it may be desirable for there to be an overlap of about 25% between different volatile materials. For instance, instead of scent "A" being emitted for 60 minutes, followed by scent "B" being emitted for 60 minutes: scent "A" can be emitted for 45 minutes; this can be followed by the emission of both scents "A" and "B" for 30 minutes; and this followed by scent "B" for 45 minutes. In this case, 30 minutes is 25% of the total time of the emission of scents "A" and "B" and the combination thereof (or 120 minutes).

The gap or overlap periods can be controlled automatically. In certain embodiments of the article(s) or device(s) used to emit the volatile materials, the article(s) or device(s) can be provided with controls to allow the user to control the duration of any gap and/or overlap in emission periods. Overlapping sequences may be used when it is desirable to have the user smell the blended scent for some period as well as distinct scents during other periods.

In certain embodiments, it is desirable for the method to be carried out by article(s) and/or device(s) that are flameless (e.g., not candles). In certain embodiments, it may also be desirable for the method to be carried out independently of other media (such other media may include, but is not limited to: movies, television, etc.). In other embodiments, it may be desirable to carry out the method in a coordinated fashion with other media.

There can be any suitable emission program or scheme for emitting the volatile compositions. In certain embodiments where scented materials are being emitted, it is desirable for the device to provide an alternating scent experience, rather than a sustained impression of a single scent. In one embodiment, it may be desirable to provide a day/night emission program where one scent is provided for waking a person, and another scent is provided for the period of time during which they are trying to go to sleep. Thus, in some embodiments, it may be desirable to deliver the same scent at the same time every day. In other embodiments, it may be desirable to avoid a routine scent experience. For example, it may be desirable for the emission pattern to not be synchronized over a 24 hour period, so that the user has a different scent experience at a given time during the day or night for each 24 hour period. Numerous other embodiments are possible.

The total emission program (or simply "the emission program") refers to the entire sequence of the discrete emission periods from beginning to end. In certain embodiments, it is desirable for the emission program to be continuous. The term "continuous", as used in reference to the emission program, means that there is a planned emission sequence over an entire period, once the program is initiated. This emission program can include periods, as noted above, where there are gaps in emission. This will still be considered to be a continuous emission program, although there will not necessarily be continuous emission of volatile compositions. It should be understood, however, that it is possible for the emission program to be interruptible by the user (e.g., turned off), if desired. Thus, the method can provide a user interface, and the user interface can provide a user with the ability to interrupt emission program. In certain embodiments, the emission program may be designed to run continuously, or substantially continuously until at least one of the volatile compositions is substantially depleted. In certain embodiments, it is desirable for the emission program to run continuously until all of the volatile compositions are substantially depleted, and for this to occur at approximately the same time. The emission program can be of any suitable length, including but not limited to 30 days, 60 days, or shorter or longer periods, or any period between 30 to 60 days.

Figure 6:
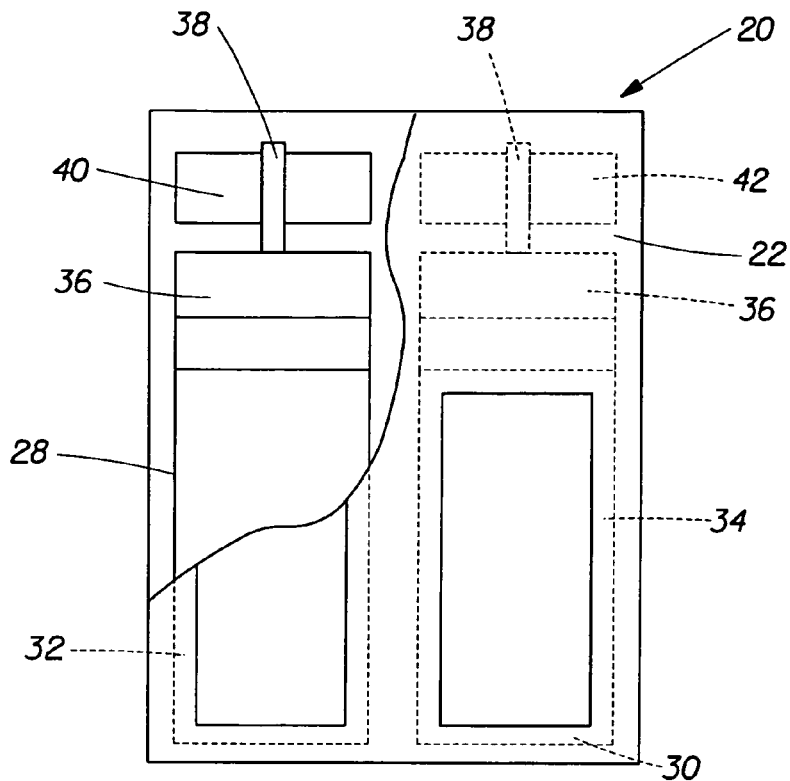
FIG. 6 is a partially fragmented schematic front view showing one non-limiting embodiment of a device for emitting volatile compositions.
Figures 7, 8:
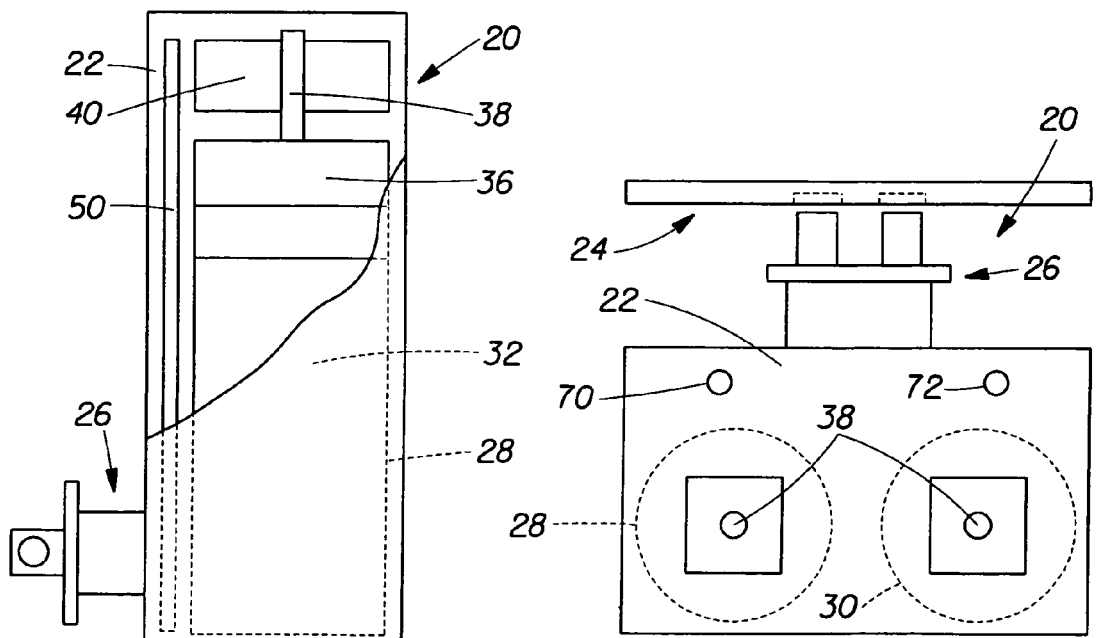
FIG. 7 is a partially fragmented schematic side view of the device shown in FIG. 6.
FIG. 8 is a schematic top view of the device shown in FIG. 6, showing the same adjacent to the cover plate of an electrical outlet.

FIGS. 6-8 show one non-limiting embodiment of a device 20 for emitting volatile compositions according to the methods described above. The device can have a pre-selected emission program which is already programmed when a consumer buys the device, or the device can be provided with a selection of several emission programs and the consumer can select between these programs. In these or other embodiments, the device 20 can use technology similar to the "random play" technology used in compact disc (CD) players to randomly alternate between different volatile materials.

As shown in FIGS. 6-8, the device 20 comprises a housing 22, and the housing 22 is supported on an electrical outlet 24 by a plug 26 that is at least indirectly joined to the housing 22. The device 20 further comprises at least one container. In the embodiment shown in FIGS. 6-8, the device 20 comprises two containers 28 and 30. The containers 28 and 30 contain at least a first volatile composition 32 and a second volatile composition 34. The housing 22 may serve as a holder for the containers 28 and 30 and any of the other components of the device described below.

The containers 28 and 30 can comprise any suitable type of container, and can be made of any suitable material. Suitable materials for the containers include, but are not limited to glass and plastic. The containers 28 and 30 can comprise any type of container that is suitable for holding volatile materials. The containers 28 and 30 may be part of the housing 22, or they may be separate components that are removably joined to a portion of the device 20 such as the housing 22. It is also possible for a single container to hold more than one type of volatile material. Such a container could, for instance, have two or more compartments for volatile materials. In the embodiment shown in FIGS. 6-8, the containers 28 and 30 comprise two separate bottles.

The bottles comprising containers 28 and 30 in FIGS. 6-8 contain volatile compositions in the form of scented perfume oils. The bottles further comprise a seal 36 for containing the volatile material, and a wick 38 for dispensing the volatile material. The device 20 and/or the bottles 28 and 30 may further comprise an additional seal for covering the wick 38 of one or more of the volatile materials when the volatile material is not being emitted.

The term "volatile compositions" as used herein, refers to a material or a discrete unit comprised of one or more materials that is vaporizable, or comprises a material that is vaporizable. The term "volatile compositions", thus, includes (but is not limited to) compositions that are comprised entirely of a single volatile material. The terms "volatile materials", "aroma", and "scents", as used herein, include, but are not limited to pleasant or savory smells, and, thus, also encompass materials that function as insecticides, air fresheners, deodorants, aromacology, aromatherapy, insecticides, or any other material that acts to condition, modify, or otherwise charge the atmosphere or to modify the environment. It should be understood that certain volatile compositions including, but not limited to perfumes, aromatic materials, and scented materials, will often be comprised of one or more volatile materials (which may form a unique and/or discrete unit comprised of a collection of volatile materials). It should be understood that the term "volatile composition" refers to compositions that have at least one volatile component, and it is not necessary for all of the component materials of the volatile composition to be volatile. The volatile compositions described herein may, thus, also have non-volatile components. It should also be understood that when the volatile compositions are described herein as being "emitted", this refers to the volatilization of the volatile components thereof, and does not require that the non-volatile components thereof be emitted. The volatile compositions of interest herein can be in any suitable form including, but not limited to: solids, liquids, gels, encapsulates, wicks, and carrier materials, such as porous materials impregnated with or containing the volatile material, and combinations thereof.

In the case of scented materials or fragrances, the different scented materials can be similar, related, complementary, or contrasting. It may not be desirable, however, for the scented materials to be too similar if the different scented materials are being used in an attempt to avoid the problem of scent habituation, otherwise, the people experiencing the scents may not notice that a different scent is being emitted. The different scents can be related to each other by a common theme, or in some other manner. For example, the different scents can all be floral, fruit scents, etc. An example of scents that are different, but complementary might be a vanilla scent and a French vanilla scent.

The present invention also comprises a method of providing choices of compatible volatile compositions, such as fragrance compositions, to consumers. In one embodiment, such a method comprises providing fragrance compositions for use in one or more emitting devices. More specifically, in one embodiment, the method can comprise providing a consumer with a selection of two or more fragrance compositions in containers that are configured for use in one or more emitting devices; and providing some type of indicia to inform a consumer which of the two or more fragrance compositions are compatible for use together. In other embodiments, containers can serve as the emitting devices (e.g., plug-in devices, aerosol cans, etc.). In certain embodiments, the method can pre-select for consumers two or more fragrance compositions that are complementary, yet discernably different. In other alternative embodiments, the method can comprise selling such different volatile compositions together, such as in bundle packs of (two, three, or more) volatile compositions. Any of the foregoing embodiments may be used in supplying consumers with their initial product(s), as well as with refills for the same. In certain embodiments, the method may comprise supplying consumers with types of volatile compositions other than, or in addition to, fragrance compositions (for example, a fragrance composition and a malodor reducing composition).

The embodiment of the device 20 shown in FIGS. 6-8 further comprises a mechanism for activating the volatile materials from their "resting" state to an activated state. Such a component may include, but is not limited to a component that volatilizes or heats the volatile materials. The device 20 may also contain a component, such as a fan, for diffusing or transporting the volatile materials into the environment or atmosphere. In various embodiments, the device 20 may comprise a heater, a fan, or both, or some other type of mechanism.

In the embodiment shown in FIGS. 6-8, the device 20 comprises at least one heating system or heater, such as heaters 40 and 42. The heaters 40 and 42 can comprise any suitable type of heater, and can be located in any suitable location in or relative to the device 20. In the embodiment shown in FIGS. 6-8, the heaters 40 and 42 comprise heating elements that are in the form of circular rings that at least partially surround the wicks 38 protruding from the bottles of the volatile compositions.

The device 20 shown in FIGS. 6-8 further comprises a switching mechanism 50 that changes the volatile material being emitted by the device 20. The switching mechanism 50 can comprise any suitable type of mechanism that causes the device to change the volatile material being emitted Lai the embodiment shown, the switching mechanism controls the activation of the heaters so that the heater will be turned on for the volatile material which is desired to be emitted. Suitable switching mechanisms include, but are not limited to: analog timing circuitry, digital circuitry, combinations of analog and digital circuitry, microprocessors, and mechanical actuation switches such as shape memory alloys (NiTi wire) or bimetallic switches.

Figure 9:
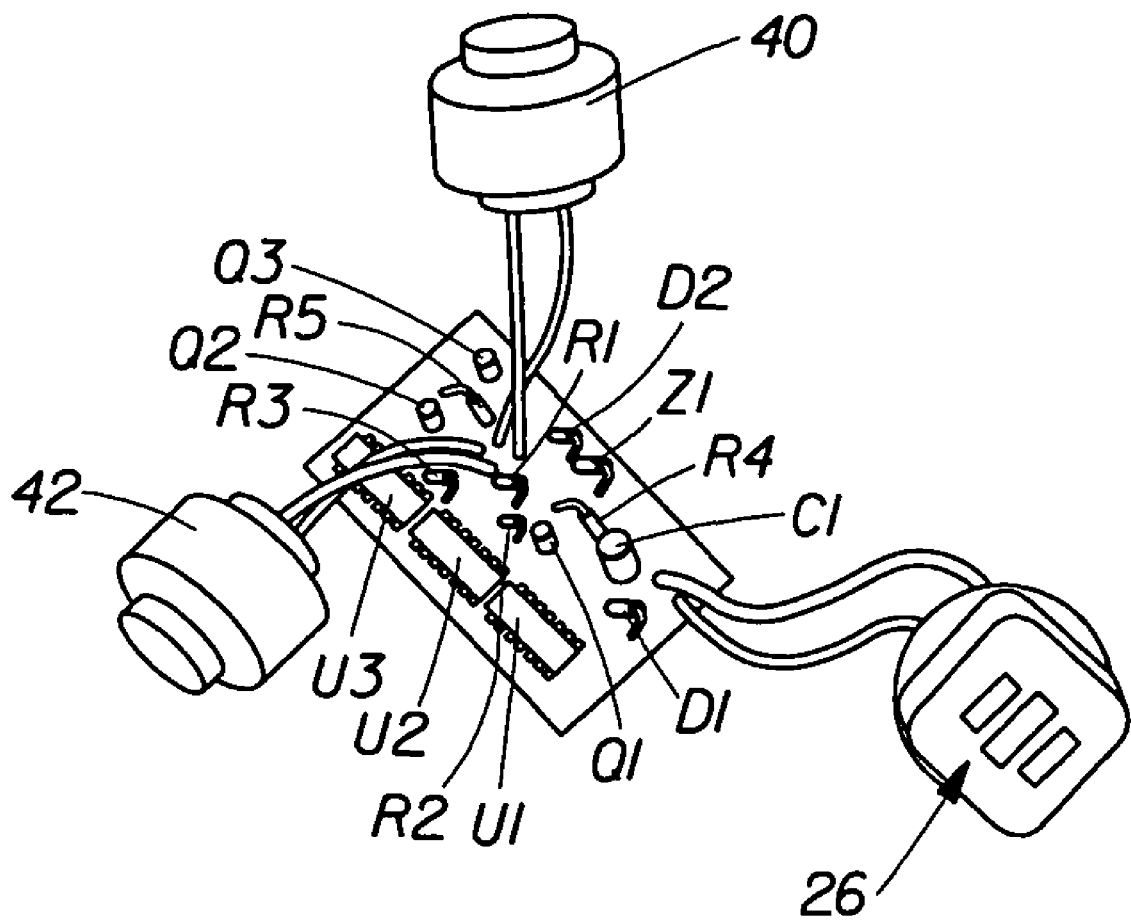
FIG. 9 is a perspective view of a printed circuit board that can be used to control the device shown in FIGS. 6-8, along with the heaters and plug that are attached thereto.

As shown in FIG. 9, in one non-limiting embodiment, the switching mechanism 50 comprises a combination analog and digital circuit in the form of a printed circuit board (or "PCB"). The circuit comprises: a single sided PC board 52; a capacitor designated C1; a pair of diodes D1 and D2; three transistors Q1, Q2, and Q3; five resistors R1-R5; three counters U1, U2, and U3; a third diode Z1. Any suitable type of heater can be used for heaters 40 and 42, including but not limited to resistance heaters (several types of which are commercially available). The heaters 40 and 42, as well as the wall power plug 26, are also connected to the circuit board 52 by wires 66. Suitable components for circuit are set out in the following table:

TABLE 1

| Reference Number or Letter | Component | Properties |
| --- | --- | --- |
| C1 | Capacitor, Electrolytic | 1 microF, 250 V |
| D1, D2 | Diode | 1N4004, or similar |
| 26 | Wall power plug | |
| Q1, Q2, Q3 | Transistors, NPN | NPN 200 V, 200 mA |
| R1-R5 | Resistors | 1/8 watt |
| U1, U2, U3 | Counters | CD4024, or similar |
| Z1 | Diode, Zener, 11 V | 1N4741A, or similar |

Figure 10:
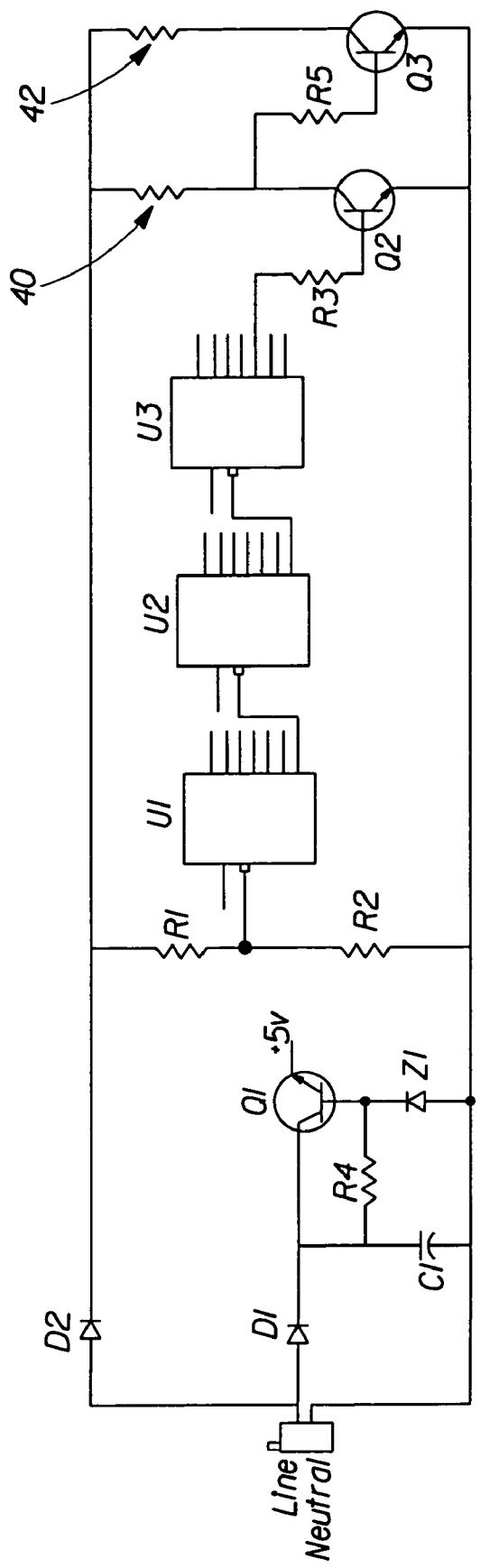
FIG. 10 is a schematic of the circuit shown in FIG. 9.

The components of the circuit may be through-hole or surface mounted. In the embodiment shown, a 38×66 mm single sided PC board 52 with through-hole components is used. The material comprising the PC board 52 can be a standard material such as FR-4 epoxy base fiberglass, but any UL approved material is acceptable. The wall power plug 26 is a molded wall plug with approximately 100 mm pigtails into the PC board. FIG. 10 is a schematic of the circuit. This circuit provides a timing function that alternates current between two paths over a time period of several tens of hours, with a pre-selected time for each heater to be turned on and off.

In other embodiments, the switching mechanism may include, but is not limited to the following alternative types of switching mechanisms: (1) a magnetic sensor with a pickup that counts the number of rotations of the motor of a fan used to disperse the volatile composition(s) such that after a certain number of rotations, the device will switch from one volatile composition to another; and (2) a device comprising dual shape memory alloys, or bimetallic strips or switches that can complete a circuit at ambient temperature and then cut-off when a certain temperature is reached. The two-way effect can be used since as the temperature lowers, the material can complete the circuit again, thus acting as a thermostat to keep the heater on and then turn it off. The shape memory alloy may serve as the heater as well as the pulse generator.

The device 20 can comprise a number of additional optional features. The device can be provided with indicators so that a person is further made aware that the volatile material being emitted has changed. Such indicators can be visual and/or audible. For example, in the case of scented materials, such an indicator may allow a person to see which scent is being emitted at a given time. In the embodiment shown in FIGS. 6-8, the indicators are in the form of lights 70 and 72. In another example, at least a portion of the device 20 (such as all or a portion of the housing) or the containers may be made of a type of plastic that changes color when heated.

The device can be provided with additional user controls. The device can comprise an "on/off" switch to allow a user to turn the device on and off without removing it from the electrical socket. The device can be provided with a control that allows the user to control the emission period of the volatile materials, and/or the time between the emission of the different volatile materials, or the time that the volatile materials are emitted during an overlapping time period. For example, in one non-limiting embodiment, if the device is provided with the capability of emitting each volatile material during a period greater than 15 minutes and less than or equal to 24 hours, then the device can be provided with a control that allows the user to set the emission period to 72 minutes, or to one hour, for example.

The device can be battery powered so that it need not be plugged into an electrical outlet. The device can also be configured so that it can be both plugged in and powered by a source of electrical current, and also battery powered. The device can also be provided with an adapter so that it can be plugged into the cigarette lighter in a vehicle. In addition, the device can be provided with a remote control that allows the user to control any, or all, of the emission properties of the device (including, but not limited to changing the volatile material being emitted) without touching the device.

The device can also be sold in the form of a kit that includes the device and one or more containers of volatile compositions. The device and/or kit can also include instructions for use that instruct the user regarding certain emission periods that may be used to produce certain results, and/or instructions regarding where to place the device in a given space. For example, the instructions may include instructions for setting the device based on the size of the room, vehicle, etc. in which the device is placed. Such instructions may also include instructions to the user to chose more frequent changes between the emission of scented materials for greater scent awareness. Instructions may also be provided to specify how to operate the device relative to other devices. The instructions can be provided in any suitable form, e.g., written, audio, and/or video.

The device may comprise a microprocessor that has less component parts compared to analog circuits, and improved circuit quality from lot to lot. The microprocessor can allow the user to program and control the temperature profile by modulation to alter performance. If desired, the microprocessor may be connected to a user interface. This can be any suitable type of user interface. Examples of types of user interfaces include, but are not limited to LCD screens and LED's. In addition, the microprocessor enables components to allow multiple devices (such as those located in different parts of a room, or in different rooms), to communicate with each other. For example, the microprocessor can enable a remote control to send digital signals via an infared beam to turn another device "on" or "off".

Figure 11:
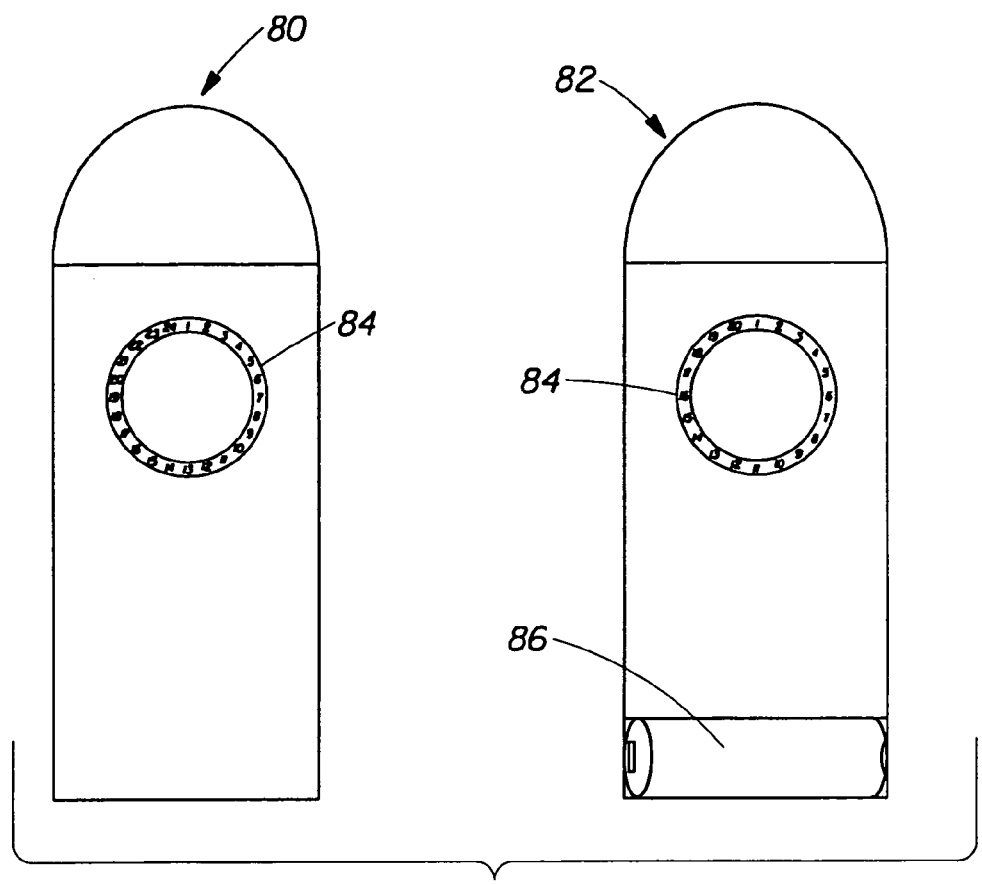
FIG. 11 shows two aerosol devices that operate on timers.
Figure 12:
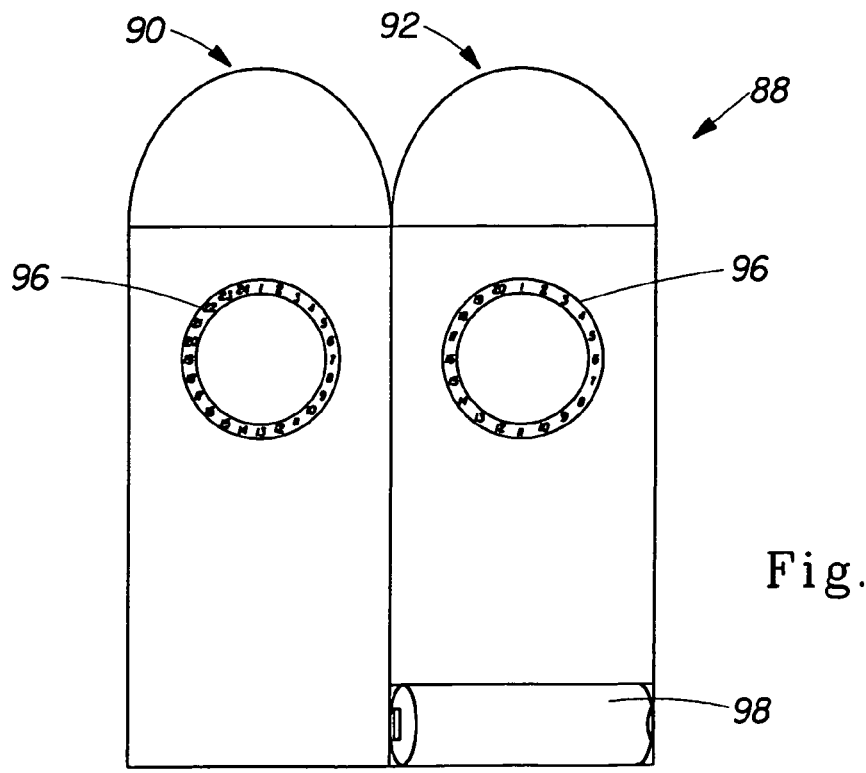
FIG. 12 shows a single device comprising two aerosol containers that operate on timers.

Numerous other types of devices are possible. For example, in other embodiments, the method described herein can be carried out by two or more dispensing devices. Such dispensing devices comprise any type of dispensing device, including, but not limited to aerosol sprayers. FIG. 11 shows one non-limiting embodiment of an arrangement of aerosol sprayers 80 and 82. The aerosol sprayers used in such a method can function in any suitable manner. In some embodiments, the aerosol sprayers may each operate independently, such as on timers 84 so that they alternate the emission of the volatile materials in the manner desired. The dispensing devices can be powered in any suitable manner, such as by a battery 86. The dispensing devices 80 and 82 may be located adjacent to each other, or they may be located in different parts of the space in which it is desired to emit the volatile materials. FIG. 12 shows another non-limiting embodiment of a dispensing device 88. In FIG. 12, the dispensing device 88 is a single device that comprises two (or more) dispensers, such as aerosol sprayers 90 and 92. The device 88 may operate on one or more timers, or sensors 96, and can be powered by one or more batteries, or other power sources.

In some embodiments, the devices can be configured to turn on and off in response to some stimulus, such as by sensors that respond to light, noise and/or motion. For example, one of the devices can be set up to turn on when it senses light, and another device can be set to turn off when it senses light. In another example, a microprocessor can be used with motion sensors to turn on the device (for example, a heater and/or a fan in the device). For example, the device can be off all the time until a person moves in the vicinity of the motion sensor. The device can then turn on when a person walks in the vicinity of the motion sensor. Using a microprocessor provides flexibility in controlling the characteristics of the emission of the volatile materials. This is because it is possible to replace the microprocessor if it is desired to change the emission characteristics. Replacing the microprocessor eliminates the need to modify the entire circuit.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

What is claimed is:

1. A system for emitting two or more volatile compositions, said system comprising at least one device wherein said two or more volatile compositions comprise a first volatile composition, a second volatile composition, and optionally additional volatile compositions, wherein said at least one device is configured to emit said first, second, and optional additional volatile compositions in a substantially continuous emission sequence in which the emission of the different volatile compositions automatically alternates between the different volatile compositions in the sequence, and further, wherein said two or more volatile compositions are contained in one or more bottles, said two or more volatile compositions are emitted using wicks, and said device comprises a timing mechanism configured to emit said volatile compositions for a discrete emission period that is greater than 35 minutes and less 120 minutes.

2. The system of claim 1 wherein at least one of said two or more volatile compositions comprises a fragrance composition.

3. The system of claim 1 wherein two or more volatile compositions comprise a fragrance composition.

4. The system of claim 1 wherein said two or more volatile compositions are emitted from a single device.

5. The system of claim 4 wherein said at least one device comprises a plug and said plug supports said at least one device on an electrical outlet.

6. The system of claim 1 wherein said at least one device comprises a single device comprising a housing, wherein said housing is supported on an electrical outlet by a plug at least indirectly joined to said housing, and said housing contains receptacles for said volatile compositions.

7. The system of claim 1 wherein said two or more volatile compositions are emitted from two or more devices.

8. The system of claim 7 wherein at least one of said devices comprises a plug that is adapted to plug into an electrical wall outlet and to support said at least one of said devices on a wall by said plug.

9. The system of claim 7 wherein said two or more devices comprise at least one aerosol sprayer.

10. The system of claim 7 wherein at least one of said two or more devices further comprises a sensor for detecting a condition for emitting at least one of said volatile compositions.

11. The system of claim 10 wherein said sensor is selected from the group consisting of: motion sensors, light sensors, and noise sensors.

12. The system of claim 7 wherein at least two of said two or more devices are configured to communicate with each other.

13. The system of claim 1 wherein said at least one device further comprises an indicator for informing the user of the device which volatile material is being emitted, wherein said indicator is selected from the group consisting of: visual and audible.

14. The system of claim 1 further comprising a control which allows a user of the device to select a desired emission period within the range of greater than 35 minutes and less than 120 minutes.

15. The system of claim 1 further comprising a control which allows a user of the device to select a desired emission period within the range of greater than or equal to about 1 hour and less than about 2 hours.

16. The system of claim 1 further comprising a control which allows a user of the device to select a desired emission period about 45 minutes.

17. The system of claim 1 wherein said timing mechanism is configured to emit said volatile compositions for a discrete emission period that is greater than or equal to about 1 hour and less than about 2 hours.

18. A device for emitting two or more volatile compositions, said device comprising a housing, wherein said housing is supported on an electrical outlet by a plug at least indirectly joined to said housing, and said housing contains receptacles for said volatile compositions wherein said two or more volatile compositions comprise a first volatile composition, a second volatile composition, and optionally additional volatile compositions, wherein said device is configured to emit said first, second, and optional additional volatile compositions in a substantially continuous emission sequence in which the emission of the different volatile compositions automatically alternates between the different volatile compositions in the sequence, and further, wherein said two or more volatile compositions are contained in one or more bottles, and said two or more volatile compositions are emitted using wicks, and further, wherein said device comprises a timing mechanism configured to emit said volatile compositions for a discrete emission period that is greater than 35 minutes and less than 120 minutes; and an indicator, the indicator being a light or a type of plastic that changes color when heated, for informing a user of said device which one of said two or more volatile compositions is being emitted.

19. The device of claim 18 further comprising a heater in said housing for volatilizing at least one of said volatile compositions.

20. The device of claim 18 further comprising a fan in said housing for dispersing at least one of said volatile compositions.

21. The device of claim 18 further comprising a heater and fan in said housing for emitting at least one of said volatile compositions.

22. The device of claim 18 wherein at least one of the volatile compositions is in a liquid form.

23. The device of claim 18 further comprising at least one heater wherein said at least one heater surrounds said wick.

24. The device of claim 23 wherein said at least one heater is operated electrically.

25. The device of claim 18 further comprising a control which allows a user of the device to select a desired emission period within the range of greater than 35 minutes and less than 120 minutes.

26. The device of claim 18 further comprising a control which allows a user of the device to select a desired emission period within the range of greater than or equal to about 1 hour and less than about 2 hours.

27. The device of claim 18 further comprising a control which allows a user of the device to select a desired emission period of about 45 minutes.

28. A system for emitting two or more volatile compositions, said system comprising:
   (a) a first device capable of emitting one or more volatile compositions comprising at least a first volatile composition;
   (b) a second device capable of emitting one or more volatile compositions comprising at least a second volatile composition; and
   (c) optional additional devices capable of emitting one or more optional additional volatile compositions;
   wherein said first, second, and optional additional volatile compositions are emitted in a substantially continuous emission sequence in which the emission of the different volatile compositions automatically alternates between the different volatile compositions in the sequence, and further, wherein said first, second, and optional additional volatile compositions are contained in one or more bottles, said two or more volatile compositions are emitted using wicks, and wherein each of said first, second, and optional additional devices comprises a timing mechanism configured to emit said first, second, and optional additional volatile compositions for a discrete emission period that is greater than 35 minutes and less than 120 minutes;
   and an indicator, the indicator being a light or a type of plastic that changes color when heated, for informing a user of said device which one of said two or more volatile compositions is being emitted.

29. The system of claim 28 further comprising a control which allows a user of the device to select a desired emission period within the range of greater than 35 minutes and less than 120 minutes.

30. The system of claim 28 further comprising a control which allows a user of the device to select a desired emission period within the range of greater than or equal to about 1 hour and less than about 2 hours.

31. The system of claim 28 further comprising a control which allows a user of the device to select a desired emission period of about 45 minutes.

* * * * *